(12) United States Patent
Marinier et al.

(10) Patent No.: US 6,194,601 B1
(45) Date of Patent: Feb. 27, 2001

(54) 5,6-DIHYDRONAPHTHALENYL DERIVATIVES HAVING RETINOID-LIKE ACTIVITY

(75) Inventors: Anne Marinier, Kirkland (CA); Yong-Jiang Hei, Bellevue, WA (US); Philippe Lapointe, Greenfield Park; Jean-Paul Daris, St.-Hubert, both of (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/397,975

(22) Filed: Sep. 16, 1999

Related U.S. Application Data

(60) Provisional application No. 60/101,609, filed on Sep. 24, 1998.

(51) Int. Cl.[7] .................................................. C07C 69/76
(52) U.S. Cl. ............................................................. 560/48
(58) Field of Search ................................. 514/513; 560/16, 560/48, 80, 102

(56) References Cited

U.S. PATENT DOCUMENTS

| 5,489,584 | * | 2/1996 | Vuligonda et al. . | |
| 5,514,825 | * | 5/1996 | Vuligonda et al. . | |
| 5,543,534 | * | 8/1996 | Vuligonda et al. . | |
| 5,599,967 | * | 2/1997 | Vuligonda et al. . | |
| 5,618,839 | * | 4/1997 | Starrett et al. . | |
| 5,618,943 | * | 4/1997 | Vuligonda et al. . | |
| 5,648,514 | | 7/1997 | Johnson et al. ...................... | 560/102 |
| 5,723,620 | * | 3/1998 | Vuligonda et al. . | |

FOREIGN PATENT DOCUMENTS

WO 97/48672 * 12/1997 (WO) .

OTHER PUBLICATIONS

Dawson et al. "Chemistry & Biology of Synthetic Retioids." CRC Press, Chapter 14; pp. 307–363 (Schiff et al.), 1996.*

* cited by examiner

Primary Examiner—Michael P. Woodward
Assistant Examiner—Sherif Kafafi
(74) Attorney, Agent, or Firm—David M. Morse

(57) ABSTRACT

The 5,6-dihydronaphthalenyl derivatives of the formulae

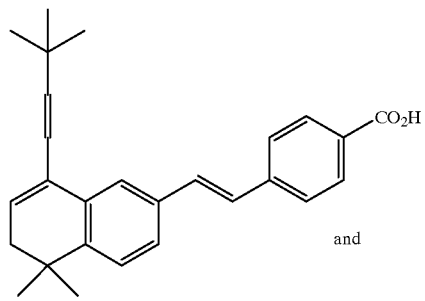

and

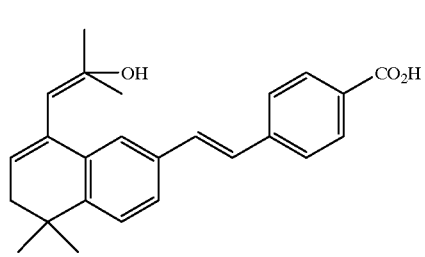

possess potent retinoid-like activity against dermatological diseases with a substantially reduced irritancy profile when administered topically.

6 Claims, 2 Drawing Sheets

5,6-DIHYDRONAPHTHALENYL DERIVATIVES HAVING RETINOID-LIKE ACTIVITY

CROSS-REFERENCE TO RELATED APPLICATION

This application claims the benefit of U.S. Provisional Application Serial No. 60/101,609 filed Sep. 24, 1998.

FIELD OF THE INVENTION

The present invention provides a series of 5,6-dihydronaphthalenyl derivatives which exhibits unexpectedly good therapeutic indexes in the treatment of skin disorders such as, but not limited to, acne and damage from age or irradiation and chronic skin inflammatory diseases such as psoriasis and atopic dermatitis. The compounds are also useful as antitumor agents for the treatment of, but not limited to, breast, skin, prostate, cervix, uterus, colon, bladder, esophagus, stomach, lung, larynx, blood and lymphatic system cancers.

BACKGROUND OF THE INVENTION

Compounds which have retinoid-like activity are well known in the art and are described in numerous patents and scientific publications. It is generally accepted that pharmaceutical compositions having a retinoid-like compound are useful for treating and/or preventing skin-related diseases such as, but not limited to acne, actinic keratosis, psoriasis, eczema and atopic dermatitis. It is also known that they are useful to reverse or treat the effects of age and photo damage to the skin and to prevent and/or treat cancerous or precancerous conditions.

One of the most significant drawbacks associated with the use of retinoids, especially in the topical treatment of dermatological diseases, is local irritation. Retinoids or compounds having retinoid-like activity that combine good topical efficacy and cutaneous tolerability are not very common. Recently, the new drug adapalene ("Differin", CIRD Galderma) was reported to offer these favorable characteristics and it has been launched in several countries as a water-based gel formulation.

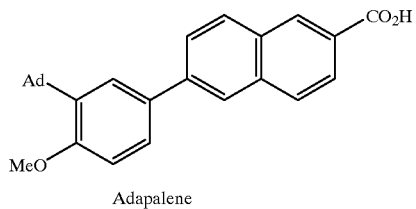

Adapalene

U.S. Pat. No. 5,648,514 describes a series of substituted (5,6)-dihydronaphthalene derivatives having retinoid-like biological activity of the formula

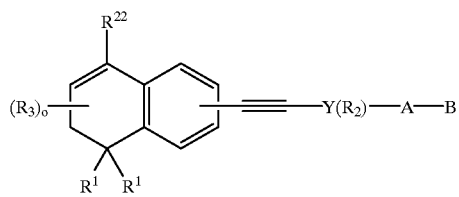

wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the dihydronaphthalene nucleus;

m is an integer having the value of 0–3;

o is an integer having the value 0–3;

Y is a phenyl group, or heteroaryl selected from a group consisting of pyridyl, thienyl, furyl, pyridazinyl, pyrimidinyl, pyrazinyl, thiazolyl, oxazolyl, and imidazolyl, said groups being optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $CH_2OH$, $CH_2OR_{11}$, $CH_2OCOR_{11}$, CHO, $CH(OR_{12})_2$, $CHOR_{13}O$, $COR_7$, $CR_7(OR_{12})_2$, $CR_7OR_{13}O$, or trilower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; and $R_{22}$ is hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$ alkyl, naphthyl-$C_1$–$C_{10}$alkyl, $C_1$–$C_{10}$-alkenylphenyl having 1 to 3 double bonds, $C_1$–$C_{10}$-alkynylphenyl having 1 to 3 triple bonds, phenyl-$C_1$–$C_{10}$alkenyl having 1 to 3 double bonds, phenyl-$C_1$–$C_{10}$alkynyl having 1 to 3 triple bonds, hydroxyalkyl of 1 to 10 carbons, hydroxyalkynyl having 2 to 10 carbons and 1 to 3 triple bonds, acyloxyalkyl of 1 to 10 carbons or acyloxyalkynyl of 2 to 10 carbons and 1 to 3 triple bonds, where the acyl group is represented by $COR_{14}$, CN, $CON(R_1)_2$, $(CH_2)_pCO_2R_8$ where p is an integer between 0 to 10, or $R_{22}$ is aminoalkyl or thioalkyl of 1 to 10carbons, or a 5 or 6 membered heteroaryl group optionally substituted with a $C_1$ to $C_{10}$ alkyl group and having 1 to 3 heteroatoms, said heteroatoms being selected from a group consisting of O, S, and N, or $R_{22}$ is represented by $(CH_2)_pXR_1$ or by $(CH_2)_pNR_1R_2$; where X is O or S, the $R_{14}$ group is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, or naphthyl-$C_1$–$C_{10}$alkyl.

That disclosure is specifically limited to the ethynyl linker. The two compounds disclosed in the present invention have the ethenyl linker. The substituent in position 8 ($R^{22}$) is defined as being, among others, an alkenyl group of 2 to 10 carbons and having 1 to 3 double bonds or an alkynyl group having 2 to 10 carbons and 1 to 3 triple bonds. This general definition does not specify the direct attachment to the dihydronaphthalene nucleus at position 8.

Published PCT patent application WO 97/48672 discloses a series of 5,6-dihydronaphthalene derivatives having retinoid and/or retinoid antagonist-like activity of the formula

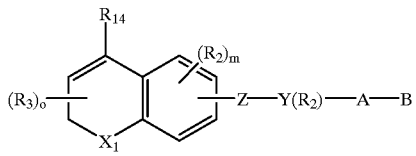

wherein $X_1$ is $[C(R_1)_2]_n$ where $R_1$ is independently H or alkyl of 1 to 6 carbons, and n is an integer between 0 and 2;

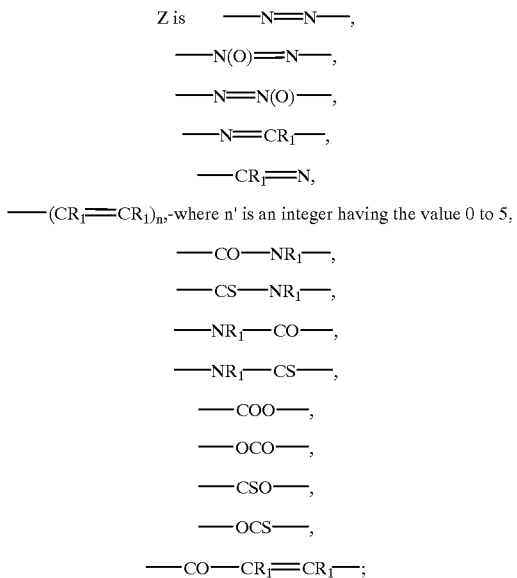

$R_2$ is hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

$R_3$ is hydrogen, lower alkyl of 1 to 6 carbons or F;

m is an integer having the value of 0 to 3;

o is an integer having the value of 0 to 3;

Y is a phenyl or naphthyl group, or heteroaryl selected from a group consisting of pyridyl, thienyl, furyl pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —$(CR_1$=$CR_1)_{n'}$— and n' is 3, 4 or 5 then Y represents a direct valence bond between said $(CR_2$=$CR_2)_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; and $R_{14}$ is $(R_{15})_r$-substituted alkyl of 1–6 carbons, $(R_{15})_r$-substituted alkenyl of 1–6 carbons and 1 or 2 double bonds, $(R_{15})_r$-substituted alkynyl of 1–6 carbons and 1 or 2 triple bonds, $(R_{15})_r$-phenyl, $(R_{15})_r$-naphthyl, or $(R_{15})_r$-heteroaryl where the heteroaryl group has 1 to 3 heteroatoms selected from the group consisting of O, S and N, r is an integer having the values of 0–5, and $R_{15}$ is independently H, F, Cl, Br, I, $NO_2$, $N(R_8)_2$, $N(R_8)COR_8$, $NR_8CON(R_8)_2$, OH, $OCOR_8$, $OR_8$, CN, COOH, $COOR_8$ and alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a (trialkyl)silyl or (trialkyl)silyloxy group where the alkyl groups independently have 1 to 6 carbons.

Two of the agents included within the scope of WO 97/48672 are the compounds having the structural formula I and II

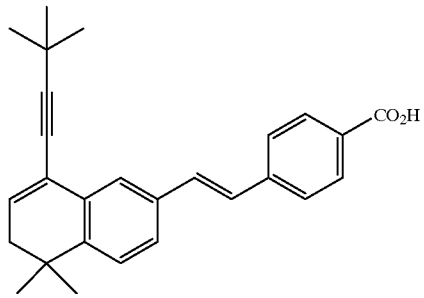

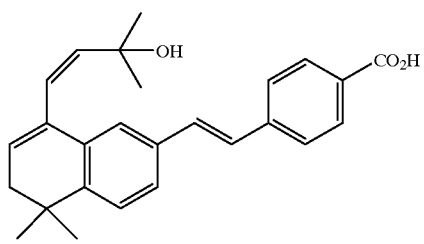

These compounds show very potent activity against dermatological diseases. Unexpectedly, the present inventors have discovered that these compounds show also a substantially reduced irritancy profile. While WO 97/48672 generally discloses these compounds as having retinoid-like activity as agents for treating skin-related diseases, there is no specific disclosure of compounds I and II or their unexpectedly low-irritation profile, which are the subject of the present invention.

In another aspect, the present inventors have also found that compounds I and II are effective tumor inhibiting agents, and thus are useful in human and/or veterinary medicine. WO 97/48672 generally discloses these compounds having retinoid-like activity and as agents for preventing or treating cancerous and precancerous conditions. The assay supporting this statement is a measure of the inhibition of 12-O-tetradecanoylphorbol-13-acetate (TPA) induction of ornithine decarboxylase (ODC) in mouse epidermis by certain compounds disclosed in application. TPA-induced ODC activity is known to occur at pre-malignant stages. Although the correlation of this assay with cellular anti-proliferation is well established, there is no evidence in the WO 97/48672 patent application of in vivo inhibition of fully established tumor growth by the disclosed compounds. The present inventors have found that the anti-proliferation activity of the compounds of this invention is translated to a potent inhibition of established tumor growth, equivalent to the most potent antitumor agents such as doxorubicin.

SUMMARY OF THE INVENTION

The present invention provides (5,6)-dihydronaphthalenyl compounds having retinoid-like activity and the structural formula

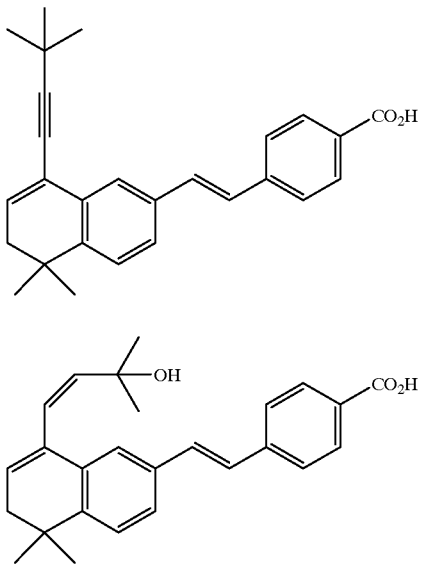

or nontoxic pharmaceutically acceptable salts, physiologically hydrolyzable esters or solvates thereof. They have unexpectedly low-irritancy profiles and are useful in the treatment of skin disorders such as, but not limited to, acne and damage from age or irradiation and chronic skin inflammatory diseases such as psoriasis and atopic dermatitis or as antitumor agents for the treatment of breast, skin, prostate, cervix, uterus, colon, bladder, esophagus, stomach, lung, larynx, blood and lymphatic system cancers.

DETAILED DESCRIPTION OF THE INVENTION

Figure 1:
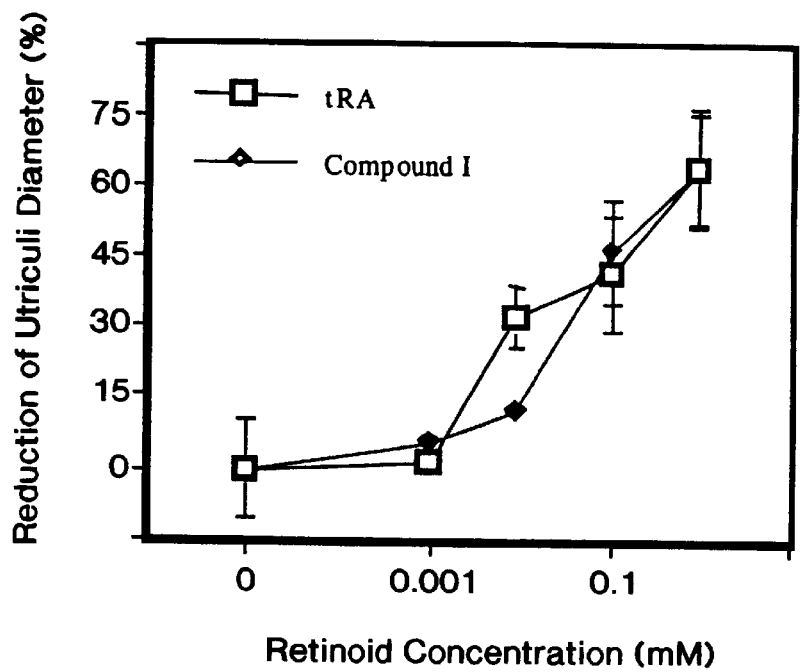
FIG. 1 shows the dose-response relationship of Compound I and tRA in the rhino mouse assay.

The present invention relates to the compounds of formula

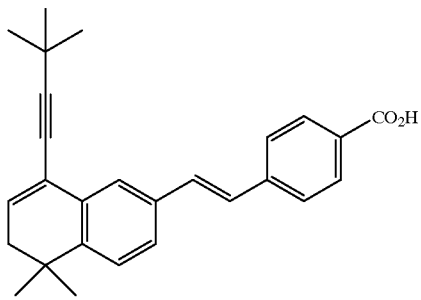

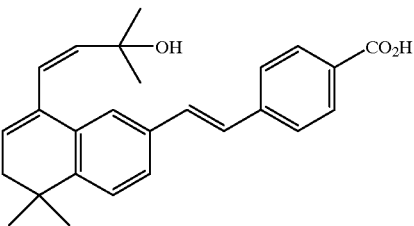

or nontoxic pharmaceutically acceptable salts, physiologically hydrolyzable esters or solvates thereof.
Definitions Compounds of formula I and 11 may form pharmaceutically acceptable metal and amine salts in which the cation does not contribute significantly to the toxicity or biological activity of the compound. These salts are part of the present invention. Suitable metal salts include the sodium, potassium, calcium, barium, zinc, and aluminum salts. The sodium or potassium salts are preferred. Amines which are capable of forming stable salts include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine, or the like.

The compounds of formula I and II can also form physiologically hydrolyzable esters which serve as prodrugs by being hydrolyzed in the body to yield formula I or II compounds per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl benzyl, 4-methoxybenzyl, indanyl, phthalyl, methoxymethyl, $C_{1-6}$ alkanoyloxy-$C_{1-6}$ alkyl, e.g. acetoxymethyl, pivaloyloxymethyl or propionyloxymethyl, $C_{1-6}$ alkoxycarbonyloxy-$C_{1-6}$ alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters are prepared by conventional techniques known in the art.

Modes of Administration

The compounds of formula I and II above may be used topically or systemically, as anticancer agents and in the treatment, amelioration or prevention of skin disorders. In this regard they may be used for therapy in mammals, including humans, of premalignant epithelial cell lesions, as a prophylaxis against tumor promotion in epithelial cells and treatment for dermatoses such as ichthyoses, follicular disorders, benign epithelial disorders and other proliferative skin diseases such as psoriasis, eczema, atopic dermatitis, non-specific dermatosis and the like. They may also be used in reversing and preventing the effects of irradiation damage to skin. When used for the above purposes, they will usually be formulated with a pharmaceutically acceptable liquid, semi-solid, or solid carrier. A pharmaceutically acceptable carrier is a material that is nontoxic and generally inert and does not adversely affect the functionality of the active ingredients. Such materials are well known and include those materials sometimes referred to as diluents or vehicles (excipients) in the pharmaceutical formulation art. The carrier may be organic or inorganic in nature. Examples of pharmaceutically acceptable carriers that may be used to formulate a compound of formula I or II are water, gelatin, lactose, starch, mineral oil, cocoa butter, dextrose, sucrose, orbital, mannitol, gum acacia, alginates, cellulose, talc, magnesium stearate, polyoxyethylene sorbitan monolaurate, and other commonly used pharmaceutical carriers. In addition to a compound of formula I or II and carrier, the formulation may contain minor amounts of additives such as flavoring agents, coloring agents, thickening or gelling agents, emulsifiers, wetting agents, buffers, stabilizers, and preservatives such as antioxidants.

The dosages and dosage regimen in which the compounds of formula I and II are administered will vary according to the dosage form, mode of administration, the condition being treated and particulars of the patient being treated. Accordingly, optimal therapeutic concentrations will be best determined at the time and place through routine experimentation.

In the treatment of dermatoses, it will generally be preferred to administer the drug topically, though in certain cases oral administration may also be used. If the compounds according to the invention are used topically, it will be found that they exhibit a good activity over a very broad range of dilution; in particular, concentrations of the active compound or compounds ranging from 0.0005% to 2% by weight can generally be used. It is of course possible to use higher concentrations if this should become necessary for a particular application; however, the preferred concentration of active principle are from 0.002% to 1% by weight.

For topical administration the compounds of formula I and II are conveniently provided in the form of unguents, gels, creams, ointments, powders, dyeing compositions, solutions, suspension, emulsions, lotions, sprays, adhesive plasters and impregnated pads. The compounds according to the invention can be mixed with inert nontoxic, generally liquid or pasty, bases suitable for topical treatment. Preparation of such topical formulations are well described in the art of pharmaceutical formulations as exemplified, for example, Remington's Pharmaceutical Science, Edition 17, Mack Publishing Company, Easton, Pa. Other medicaments can be added to such formulation for such secondary purposes as treating skin dryness, providing protection against light; other medications for treating dermatoses, preventing infection, reducing irritation, inflammation and the like.

The compounds according to the invention can also be used enterally. Orally, the compounds according to the invention are suitable administered at the rate of 100 mg to 100 mg per day per kg of body weight. The required dose can be administered in one or more portions. For oral administration, suitable forms are, for example, tablets, pills, dragees, syrups, suspensions, emulsions, solutions, powders and granules; a preferred method of administration consists in using pills containing from 1 mg to about 1000 mg of active substance.

U.S. Pat. No. 4,876,381 issued on Oct. 24, 1989 to Lang et al. provides examples of formulations constituting gel, unguent, powder, cream, etc. The aforesaid U.S. patent can be used as a guide to formulate a compound of formula I and II and is hereby incorporated by reference in its entirety.

Isotretinoin (Accutane") and etretinate (Tegison") are used clinically to treat severe recalcitrant cystic acne and severe recalcitrant psoriasis, including the erythrodermica and generalized pustular types, respectively. Their mode of use is amply illustrated in the *Physician's Desk Reference,* 47th Edition (1993), published by Medical Economics Data. The compounds of formula I and II may also be used to treat severe recalcitrant psoriasis. In so doing, the compounds of the present invention may be used in a similar fashion to isotretinoin and etretinate; thus, the relevant sections on isotretinoin and etretinate in the *Physician's Desk Reference* will serve as a convenient guide which will obviate the need for any undue experimentation.

The compounds according to the invention can also be administered parenterally in the form of solutions or suspensions for intravenous or intramuscular perfusions or injections. In that case, the compounds according to the invention are generally administered at the rate of about 10 mg to 10 mg per day per kg of body weight; a preferred method of administration consists of using solutions or suspensions containing approximately from 0.01 mg to 1 mg of active substance per Several retinoids have been found to possess anti-tumor properties. Roberts, A. B. and Sporn, M. B. in *The Retinoids,* Sporn, M. B., Roberts, A. B., and Goodman, D. S., eds., 2, p. 209–286 (1984), Academic Press, New York; Lippman, S. M., Kessler, J. F., and Meyskens, F. L., *Cancer Treat. Rep.,* 71, p. 391 (1987); ibid., p. 493. As used herein, the term "anti-tumor" includes both chemopreventive (prophylactic or tumor promotion inhibiting) and therapeutic (curative) use. For example, all-trans retinoic acid can be used to treat acute promyelocytic leukemia. Huang, M. Et al., *Blood,* 72, p. 567 (1988). Isotretinoin has been shown to be useful in prevention of second primary tumors in squamous-cell carcinoma of the head and neck. Hong, W. K. et al., *N. Engl. J. Med.,* 323, p. 795 (1990).

The compounds of formula I and II can be used in a substantially similar manner to retinoids for treating (both chemopreventively and therapeutically) various tumors. For the compounds of this invention, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. An oncologist skilled in the art of cancer treatment will be able to ascertain, without undue experimentation, appropriate protocols for the effective administration of the compounds of this present invention, such as by referring to the earlier published studies on retinoids found to have anti-tumor properties. For example, for the prevention of second primary tumors with a compound of formula I and II in squamous-cell carcinoma of the head and neck, an oncologist may refer to the study by Hong, W. K. et al. in *N. Engl. J. Med.,* 323, p. 795 (1990). For treating acute promyelocytic leukemia, the oncologist may refer to the study by Huang, M. et al. in *Blood,* 72, p. 567 (1988).

Biological Activity

The retinoid-like activity and efficacy of these compounds has been confirmed by a retinoid transactivation assay described in *Skin Pharmacology*, 8, p. 292–299 (1995). HeLa cells are co-transfected with DNA encoding RARα, β or γ, and an RAR-responsive CAT reporter gene. Retinoid efficacy is measured by the concentration of induced CAT gene product as determined by ELISA assay. The compounds of the present invention have shown activity as agonist or partial agonist in at least one of the three receptor subtypes (α, β, γ). The apparent Kds for binding of these compounds to the three RAR receptors have been also evaluated by an assay described in *Skin Pharmacology*, 8, p. 292–299 (1995) and *Mode of Action of Drugs on Cells*, Arnold Publishers, London (1933) and Table 1 shows the data of the compounds I and II.

TABLE 1

| Compound | Kd (α) nM | Kd (β) nM | Kd (γ) nM |
|---|---|---|---|
| I | 2.23 | 1.26 | 25 |
| II | 1.60 | 2.19 | 1.57 |
| TRA* | 0.6 | 0.6 | 0.28 |

*All-trans retinoic acid

The comedolytic activity of the compounds of the instant application has been evaluated by the rhino mouse assay model. The compounds were administered daily to rhino mice topically in ethanol at various concentrations for 5 days. Signs of skin irritation are evaluated at day 5 by visual inspection of the mouse skin and graded for edema, erythema (redness) and scaling (flakiness) with scales of 1–5 and 1–4, respectively. Skin samples were taken at day 7 and processed for image analysis to measure the size of utriculi.

Table 2 provides the percent of inhibition at two different concentrations of the compounds I and II of the present invention as well as some other compounds generically disclosed by the patent application WO 97/48672.

TABLE 2

[Structure: tetrahydronaphthalene with R and R' substituents connected via CH=CH to benzoic acid ($CO_2H$)]

| Compound | R' | R | Utriculi reduction at 1 mM | Utriculi reduction at 0.1 mM |
|---|---|---|---|---|
| I | H | —≡—tBu | 100% | 72% |
| II | H | cis-CH=CH—C(CH$_3$)$_2$OH | 84% | 8.4% |
| A | Me | —≡—tBu | NT** | 100% |
| B | H | cis-CH=CH—C(Et)$_2$CH$_3$ | 100% at 1.6 mM | NT** |
| C | H | cis-CH=CH-tBu | NT** | 30% at 0.01 mM |
| D | H | SCH(CH$_3$)$_2$ | NT** | 85.4% |
| TRA* | | | 100% | 64% |

*All-trans retinoic acid
**not tested

No irritation was observed for compound I at concentrations up to 10 mM. The positive control drug, all-trans retinoic acid (tRA), caused an erythema grade of 4.8 and a scaling grade of 2.5 at 1 mM. The pharmacological activity in reducing utriculi size is shown in FIG. 1. The potency of the compounds is determined by ED30 values which are the doses at which 30% reduction in utriculi size is achieved. This is equivalent to ED50 in other studies since the maximum achievable utriculi reduction in this model is ~60%. Compound I has a ED30 value of 0.055 mM as compared to tRA with a ED30 value of 0.028 mM in this study.

The irritation study of the retinoid compounds of this invention was also performed with a more sensitive animal model, i.e., the rabbit skin irritation model. In this model, the compounds were applied topically daily to rabbit skin for 14 days in ethanol vehicle. The animals were graded daily for signs of irritation, i.e., edema, erythema and scaling, which are typical of retinoid effects on the skin. The total irritation score over the 14 day period was used to obtain the area under the curve (AUC).

Table 3 shows the erythema score of the compounds I and II of the present invention, as well as the erythema score of some other compounds generically disclosed in the patent application WO 97/48672. It can be noticed that for compounds I and II, the irritation and inflammation usually seen with retinoids administered topically, was not observed. It is worthy of note that many other compounds of the patent application WO 97/48672 were found to be irritating. This demonstrates that the compounds of the present invention are unexpectedly devoid of skin irritation which is not a common characteristic of compounds having retinoid-like activity and could not be predicted for such compounds.

TABLE 3

[Structure: tetrahydronaphthalene with R and R' substituents connected via CH=CH to benzoic acid ($CO_2H$)]

| Compound | R' | R | Erythema score |
|---|---|---|---|
| I | H | —≡—tBu | 0 |
| II | H | cis-CH=CH—C(CH$_3$)$_2$OH | 0 |
| A | Me | —≡—tBu | 3.1 |
| B | H | cis-CH=CH—C(Et)$_2$CH$_3$ | 2.8 |
| C | H | cis-CH=CH-tBu | 6.0 |
| D | H | —SCH(CH$_3$)$_2$ | 5.7 |
| TRA* | — | — | 4.8 |

*All-trans retinoic acid

Figure 2:
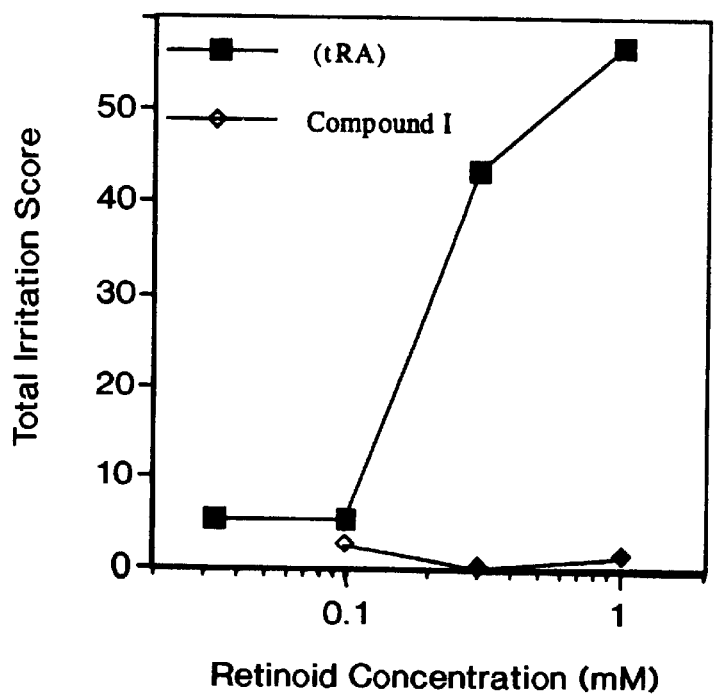
FIG. 2 shows the results of the rabbit skin irritation study.

The total irritation score over the 14 day period was used to obtain the area under the curve (AUC) for Compound I and tRA at different doses and is shown in FIG. 2. Clearly tRA caused significant irritation to rabbit skin at concentrations above 0.1 mM, while Compound I did not cause any irritation at 1 mM. At even higher dose (5 mM), Compound I did not cause any signs of irritation to rabbit skin.

The compounds of the present invention have been also tested as inhibitors of cell proliferation ($^3$H-thymidine uptake). Cells were plated on 96-well plates at a predetermined density so that 80% cellular confluency is reached by day 7. 24 hr after plating, culture media was changed and cells were treated with the appropriate drug or vehicle (day 0). Culture media was changed on days 3 and 6. Cellular proliferation was measured on Day 7 by quantitating the amount of tritiated thymidine ([3H]-TdR) incorporated into the celular DNA (Odham, K. G. (1977) in: *Radiotracer Techniques and Applications*, edited by E. A. Evans and M. Murawatsu; M. Dekker Inc. New York; 2, 823).

Table 4 shows the ED30 values of topical activity as well as a measure of the concentration necessary to achieve an irritation score of 3 (IS3) for the compounds I and II of the present invention and the compounds generically disclosed in the patent application WO 97/48672. Compound I, which did not show any signs of irritation at 5 mM has a therapeutic index highly superior to TRA and to most of the closely related analogs disclosed in WO 97/48672. Compound I of the present invention, unlike its closely related analogs is unexpectedly unique in that aspect.

TABLE 4

| Compound | R' | R | $ED_{30}$ (mM) | IS3 (mM) | Therapeutic index |
|---|---|---|---|---|---|
| I | H | —tBu | 0.055 | No irritation in rabbits at 5 mM | >>99 |
| II | H | cis-CH=CH—C(CH$_3$)$_2$OH | 0.4 | No irritation in rhino mice | |
| A | Me | —tBu | <0.1 | Very irritating in rhino mice (>>TRA) | |
| B | H | cis-CH=CH—C(Et)$_2$CH$_3$ | | Irritating (<TRA) | |
| C | H | cis-CH=CH-tBu | 0.08 | Very irritating to rhino mice and rabbits | <20 |
| D | H | SCH(CH$_3$)$_2$ | <0.1 | Very irritating (>>TRA) | |
| TRA | | | 0.015 | 0.3 | 20 |

Table 5 provides the $IC_{50}$ values of some representative compounds in various carcinoma cell lines. The compounds of the present invention showed potent anti-proliferative activity.

This potent anti-proliferative activity is also translated in vivo on athymic mice bearing H3396 (ER+) breast carcinoma subcutaneous xenografts (P. A. Trail, et al., *Cancer Research*, 52, p. 5693–5700 (1992). Athymic mice were implanted with 0.72 mg (60-day release) estradiol pellets (Innovative Research of America, Toledo, Ohio) one day prior to the implantation of H3396 tumors. H3396 tumors were measured in two perpendicular directions at weekly or biweekly intervals, using calipers. Tumor volume was calculated according to the equation: $V=I \times w^2/2$, where V=volume (mm3), I=measurement of longest axis (mm), and w=measurement of axis perpendicular to 1. In general, there were 8–10 mice in each control or treatment group. Data are presented as median tumor size for control or treated groups. Antitumor activity is expressed in terms of median TVDD values, where TVDD=T–C/TVDT; T–C is defined as the median time (days) for treated tumors to reach 500 mm3 in size minus the median time for control tumors to reach 500 mm3 in size and TVDT is the time (days) for control tumors to double in volume (250–500 mm3).

Figure 3:
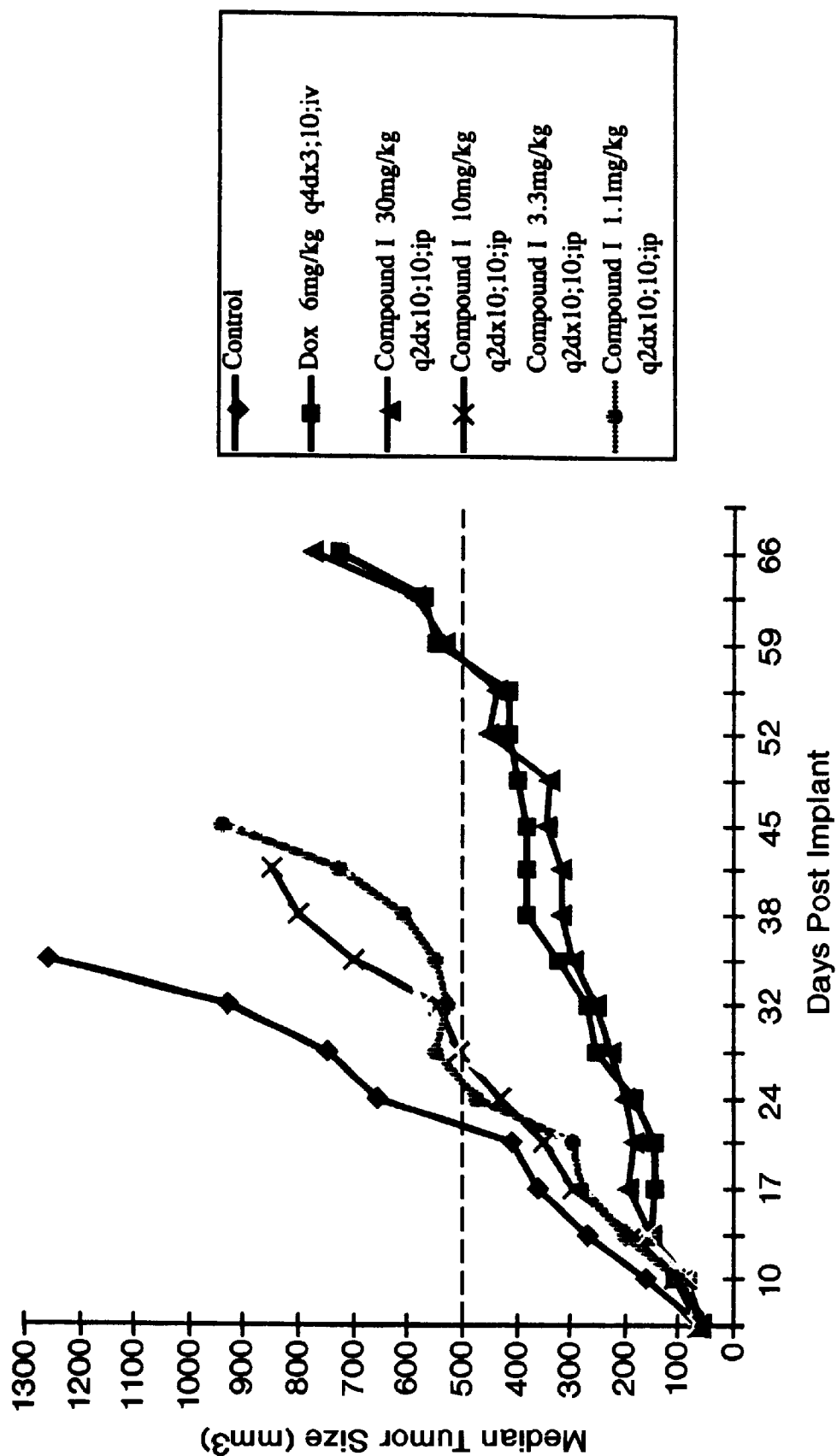
FIG. 3 shows the inhibition of tumor growth upon ip administration of Compound I.

Compound I, when administered intraperitoneally every two days for 10 days, is as potent as doxorubicin in that model in inhibiting tumor growth as shown in FIG. 3 and Table 5. In this experiment, the tumor growth delay was equivalent to 1.2 log cell kill at 30 mg/kg.

DESCRIPTION OF THE SPECIFIC EMBODIMENTS

The synthesis of the compounds of the present invention can be accomplished by a wide variety of methods using conventional starting materials and processes. The synthetic descriptions and specific examples that follow are only intended for the purpose of illustration, and are not to be construed as limiting in any manner preparation of compounds of the present invention by other methods.

The preparation of the compounds of the present invention as well as the related analogs is described in Schemes 1 and 2. The tetralone III described in U.S. Pat. No. 5,648,385 (Scheme 1), was converted to the corresponding vinyl triflate V as disclosed in WO 97/48672. This triflate was then treated with various acetylenes or tin derivatives under Heck or Stille conditions to afford the 8-substituted dihydronaphthalene compounds IVb, d or e. Reduction of

TABLE 5

| Compound No. | R | SK-BR-3 Breast CA (E2-indep.) $IC_{50}$ (μM) | H3396 Breast CA (E2-dep.) $IC_{50}$ (μM) | MCF7 Breast CA (E2-dep.) $IC_{50}$ (μM) | Calu-3 Lung CA $IC_{50}$ (μM) | Detroit 562 Pharyngeal CA $IC_{50}$ (μM) | SCC 25 tongue SCC $IC_{50}$ (μM) |
|---|---|---|---|---|---|---|---|
| I | —≡—tBu | 0.008 | 0.04 | 6.5 | 0.01 | 5.5 | 9.5 |
| II | cis-CH=CH—C(CH$_3$)$_2$OH | | | | | | |
| TRA* | — | 0.001 | 0.3 | 0.65 | 0.1 | >10 | 0.05 |

*All-trans retinoic acid the acetylenes IVb and IVd gave respectively the cis olefins IVc and IVf. The tetralone III was also reacted with isopropylthiol in presence of titanium chloride to produce the vinyl isopropylsulfide IVa.

To prepare the 7-methyl analog A, the tetralone VI (Scheme 2) described in U.S. Pat. No. 5,648,385 was alkylated using methyltriflate and then coupled to methyl p-vinylbenzoate under Heck conditions to give the 7-methylated tetralone VIII. Conversion of the ketone to the corresponding vinyl triflate was then followed by the usual Heck coupling with t-butylacetylene and produced the 8-substituted dihydronaphthalene derivative IVg.

The 8-substituted 5,6-dihydronaphthalene compounds IVa to g were then saponified under the usual conditions to afford the compounds of the present invention I and II and the analogs A, B, C and D.

SCHEME 1
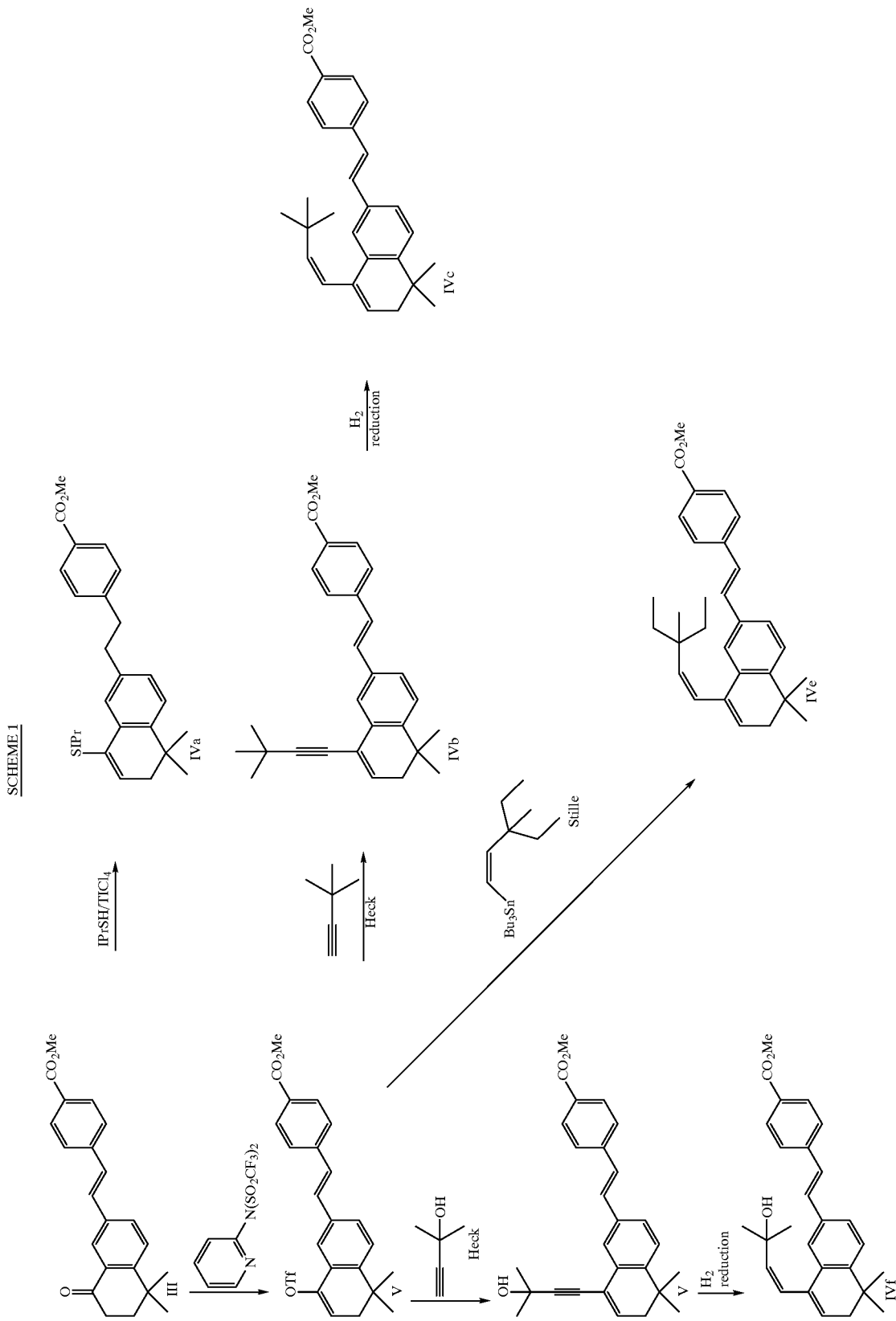

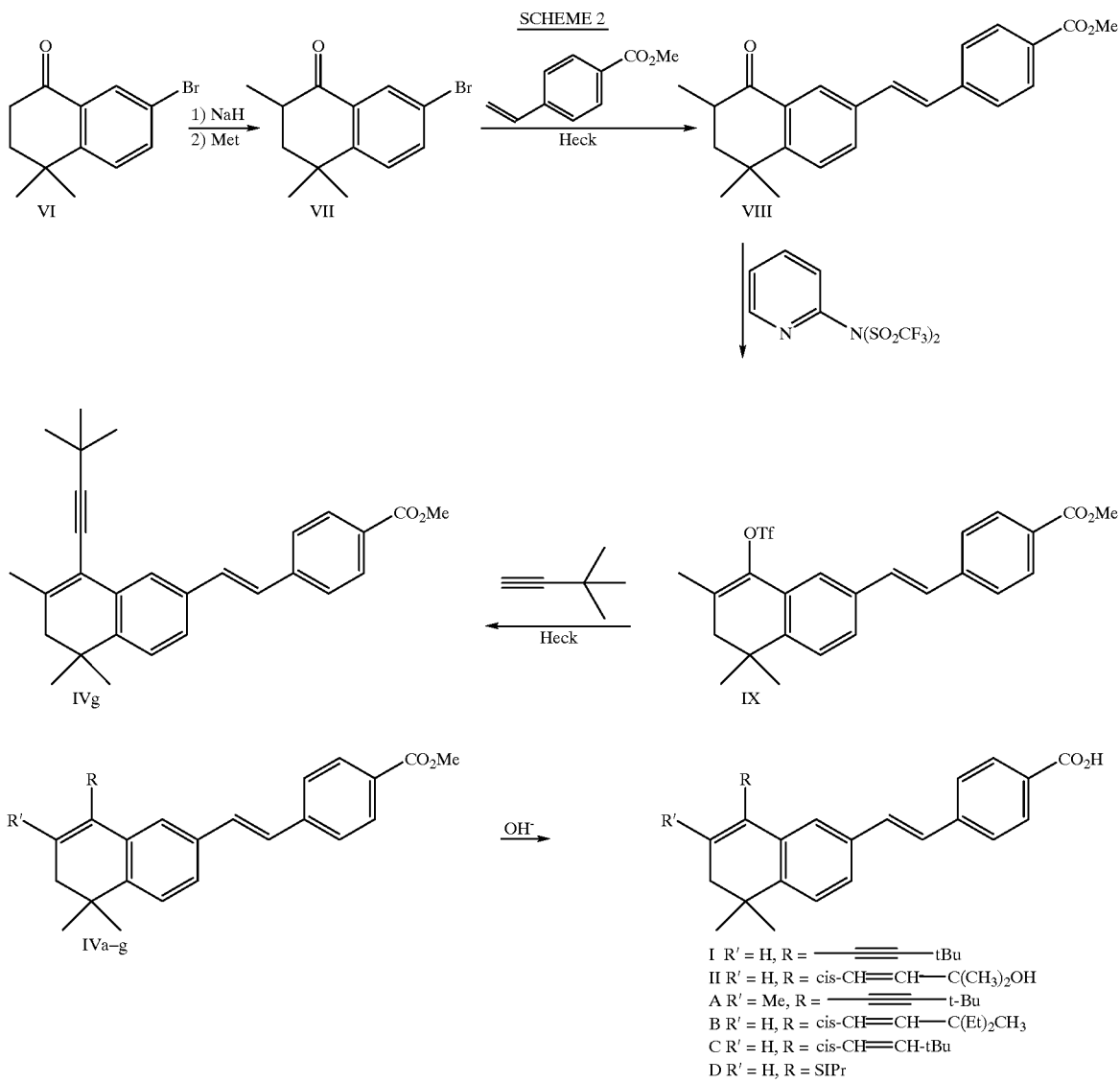

SCHEME 2

DESCRIPTION OF THE SPECIFIC EXAMPLES

Analytical grade solvents were used for reactions and chromatographies. Flash column chromatographies were performed on Merck silica gel 60 (230–400 Mesh) and Merck silica gel 60 $F_{254}$ 0–5 mm plates were used. All melting points were determined on a Gallenkamp metling point apparatus and were not corrected. $^1$H NMR spectra were measured on a Bruker AMX400 (400 MHz) instruments. Chemical shifts were reported in δ units using the solvent as internal standard. The signals are described as s (singlet), d (doublet), t (triplet), qa (quartet), qi (quintet), m (multiplet) and br (broad). Infrared spectras were recorded on a Perkin-Elmer 781 and optical rotations were measured on a Perkin-Elmer 241 apparatus.

Example 1

4-[(E)-(5,6-Dihydro-5,5-dimethyl-8-(3,3-dimethyl-1-butyn-1-yl)-2-naphthalenyl)ethenyl]benzoic acid

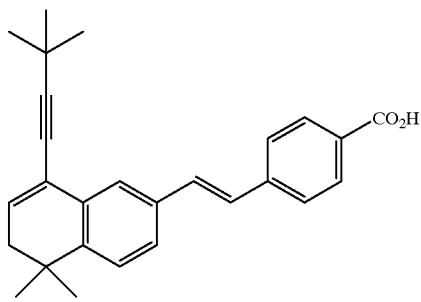

Methyl 4-[(E)-[5,6-dihydro-5,5-dimethyl-8-trifluoromethanesulfonyloxy-2-naphthalenyl]ethenyl]benzoate A solution of methyl 4-[[(E)-(5,6,7,8-tetrahydro-5,5-dimethyl-8-oxo)-2-naphthalenyl]vinyl]benzoate (U.S. Pat. No. 5,618,839 and EP 661,259 A1) (10.02 g, 30 mmol) in tetrahydrofuran (200 mL) at −78° C. was treated dropwise with a solution of lithium bis(trimethylsilyl)amide (1.0M in tetrahydrofuran, 42 mL, 42 mmol). The solution was stirred for 30 minutes then treated with a solution of 2-[N,N-bis(trifluoromethylsulfonyl)amino]pyridine (14 g, 39 mmol) in tetrahydrofuran (100 mL). The mixture was stirred overnight and was allowed to reach room temperature. The mixture was cooled to 0–5° C., diluted with water (200 mL) and ethyl acetate (200 mL). The organic phase was separated and the aqueous phase was extracted with ethyl acetate (100 mL). The combined organic phases were washed with brine and dried over anhydrous magnesium sulfate, filtered and concentrated. The residue was purified by silica gel chromatography (toluene to toluene/ethyl acetate 8:2) and triturated in hexanes to give the title material (10.5 g, 75%) as a white solid.

$^{1}$H NMR 400 MHz (CDCl$_3$) δ (ppm): 1.34 (6H, s,2x—CH$_3$), 2.45 (2H, d, J=4.8 Hz, H-6'), 3.94 (3H, s, —OCH$_3$), 6.02 (1H, t, J=4.8 Hz, H-7'), 7.13 (1H, d, J=16.3 Hz, vinyl H), 7.22 (1H, d, J=16.3 Hz, vinyl H), 7.34 (1H, d, J=8.0 Hz, H-4'), 7.51 (1H, dd, J=8.0 and 1.6 Hz, H-3'), 7.54 (1H, br s, H-1'), 7.59 (2H, d, J=8.3 Hz, H-3 and H-5), 8.05 (2H, d, J=8.4 Hz, H-2 and H-6).

Methyl 4-[(E)-(5,6-dihydro-5,5-dimethyl-8-(3,3-dimethyl-1-butyn-1-yl)-2-naphthalenyl)ethenyl]benzoate To a cold (5° C.) solution of 4-[(E)-[5,6-dihydro-5,5-dimethyl-8-trifluoromethanesulfonyloxy-2-naphthalenyl]ethenyl]benzoate (13.73 g, 29.46 mmol) in tetrahydrofuran (200 mL) was added, in order, dimethylbutyne (6.05 g, 73.65 mmol, 9.07 mL), bistriphenylphosphinepalladium(ll) chloride (250 mg), cupper iodide (1.4 g, 7.37 mmol) and diisopropylamine (30 mL). The reaction mixture was stirred at 5° C. for 2 hours, then diluted with ethyl ether and washed with water, 1N hydrochloric acid and brine. The organic layer was dried over anhydrous magnesium sulfate, filtered and concentrated. A brownish solid was obtained which was triturated in ethyl ether/hexane and gave the title compound (5.9 g, 50%). The filtrate was concentrated and the residue was purified by silica gel chromatography (0–10% ethyl acetate/hexane) to give an additional quantity of the title compound (4.37 g, 37%). Some impure material (>1 g) was discarded.

IR (KBr) $v_{max}$ (cm$^{-1}$): 2985, 1715 (C═O), 1605.

$^{1}$H NMR 400 MHz (CDCl$_3$) δ (ppm): 1.30 (6H, s, 2x—CH$_3$),1.42 (9H, s, —tBu), 2.32 (2H, d, J=4.8 Hz, H-6'), 3.94 (3H, s, —OCH$_3$), 6.33 (1H, t, J=4.8 Hz, H-7'), 7.13 (1H, d, J=16.3 Hz, vinyl H), 7.23 (1H, d, J=16.3 Hz, vinyl H), 7.30 (1H, d, J=7.9 Hz, H-4'), 7.39 (1H, dd, J=7.9 and 1.7 Hz, H-3'), 7.56 (2H, d, H-3 and H-5), 7.85 (1H, d, J=1.6 Hz, H-1'), 8.04 (2H, d, J=8.3 Hz, H-2 and H-6).

| Anal. Calcd. for C$_{28}$H$_{30}$O$_2$: | C 84.38; H 7.59. |
|---|---|
| Found: | C 83.95; H 7.69. |

4-[(E)-(5,6-Dihydro-5,5-dimethyl-8-(3,3-dimethyl-1-butyn-1-yl)-2-naphthalenyl)ethenyl]benzoic acid A solution of methyl 4-[(E)-(5,6-dihydro-5,5-dimethyl-8-(3,3-dimethyl-1-butyn-1-yl)-2-naphthalenyl)ethenyl]benzoate (3.0 g, 7.53 mmol) in a mixture of tetrahydrofuran/ethanol (1:1, 60 mL) was treated with 4N sodium hydroxide (9.4 mL, 32.64 mmol) and stirred at room temperature for 20 h. Then the reaction mixture was diluted with water (100 mL) and acidified to pH=1 with concentrated hydrochloric acid. The precipitate was extracted with ethyl acetate and the extracts were washed with water, dried over anhydrous magnesium sulfate and evaporated. The resulting solid was dissolved in dichloromethane/ethanol (150 mL//100 mL) and the solution was filtered through a sintered glass and the filtrate was concentrated. Upon concentration, the title compound crystallized out and was collected and dried to give 2.62 g (90%) of the title material as a white solid.

IR (KBr) $v_{max}$ (cm$^{-1}$): 3650–2000 (br), 2825, 1670 (C═O), 1600.

$^{1}$H NMR 400 MHz (DMSO-d$_6$) δ (ppm): 1.22 (6H, s, 2x—CH$_3$), 1.37 (9H, s, —tBu), 2.28 (2H, d, J=4.8 Hz, H-6'), 6.31 (1H, t, J=4.8 Hz, H-7'), 7.20 (1H, d, J=16.4 Hz, vinyl H), 7.36 (1H, d, J=8.0 Hz, H-4'), 7.41 (1H, d, J=16.4 Hz, vinyl H), 7.55 (1H, dd, J=8.0 and 1.7 Hz, H-3'), 7.71 (2H, d, J=8.3 Hz, H-3 and H-5), 7.72 (1H, br s, H-1'), 7.94 (2H, d, J=8.3 Hz, H-2 and H-6).

| Anal. Calcd. for C$_{27}$H$_{28}$O$_2$: | C 84.34; H 7.34. |
|---|---|
| Found: | C 84.22; H 7.23. |

Example 2

4-[(E)-(5,6-Dihydro-5,5-dimethyl-8-((Z)-3-methyl-3-hydroxyl-1-buten-1-yl)-2-naphthalenyl)ethenyl] benzoic acid

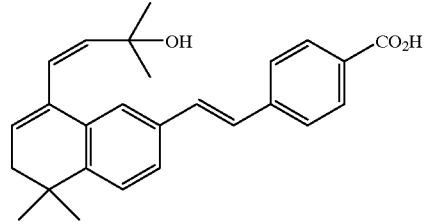

Methyl 4-[(E)-(5,6-dihydro-5,5-dimethyl-8-(3-methyl-3-hydroxyl-1-butyn-1-yl)-2-naphthalenyl)ethenyl]benzoate A solution of methyl 4-[(E)-[5,6-dihydro-5,5-dimethyl-8-trifluoromethanesulfonyloxy-2-naphthalenyl]ethenyl]benzoate (0.350 g, 0.75 mmol) was reacted as described in Example 1 by using 3-methyl-3-hydroxyl-1-butyne (0.158 g, 1.88 mmol, 0.18 mL) and tetrakistriphenylphosphinepalladium(0) and gave the title material (0.295 g, 98%) which was crystallized from ethyl ether at −20° C.

IR (CH$_2$Cl$_2$) $v_{max}$ (cm$^{-1}$): 1716 (C═O), 1604.

$^{1}$H NMR 400 MHz (CDCl$_3$) δ (ppm): 8.04 (2H, d, J=8.3 Hz, H-2 and H-6), 7.76 (1H, br s, H-1'), 7.57 (2H, d, J=8.3 Hz, H-3 and H-5), 7.43 (1H, br d, J=8.0 Hz, H-3'), 7.32 (1H, d, J=8.0 Hz, H-4'), 7.23 and 7.12 (2x1H, 2 d, J=16.3 Hz, vinyl H), 6.42 (1H, t, J=4.8 Hz, H-7'), 3.94 (3H, s, —OCH$_3$), 2.34 (2H, d, J=4.8 Hz, H-6'), 2.05 (1H, br s, —OH), 1.71 (6H, s, 2x—CH$_3$), 1.30 (6H, s, 2x—CH$_3$).

Methyl 4-[(E)-(5,6-dihydro-5,5-dimethyl-8-((Z)-3-methyl-3-hydroxy-1-buten-1-yl)-2-naphthalenyl)ethenyl]benzoate A mixture of methyl 4-[(E)-(5,6-dihydro-5,5-dimethyl-8-(3-methyl-3-hydroxy-1-butyn-1-yl)-2-naphthalenyl)ethenyl]benzoate (0.228 g, 0.57 mmol) and 10% Pd/BaSO$_4$ (75 mg) in pyridine (5 mL) was hydrogenated (rubber balloon) for 60 minutes at room temperature. The reaction mixture was then filtered through celite and the pad washed with ethyl ether. The filtrate was washed with water, 1N hydrochloric acid and brine, dried over magnesium sulfate, filtered and concentrated. The residue was purified on silica gel chromatography (dichloromethane/acetonitrile) to give the title material (135 mg, 59%) as a white solid.

$^1$H NMR 400 MHz (CDCl$_3$) δ (ppm): 8.03 (2H, d, J=8.3 Hz, H-2 and H-6), 7.58 (2H, d, J=8.3 Hz, H-3 and H-5), 7.43 (1H, dd, J=8.0 and 1.8 Hz, H-3'), 7.39 (1H, d, J=1.6 Hz, H-1'), 7.35 (1H, d, J=7.9 Hz, H-4'), 7.21 and 7.08 (2×1H, 2 d, J=16.3 Hz, vinyl H), 6.15 (1H, dq, J=12.4 and 2.1 Hz, —CH̲=CH(CH$_3$)$_2$OH), 5.98 (1H, m, H-7'), 5.91 (1H, d, J=12.4 Hz, —CH=CH̲(CH$_3$)$_2$OH), 3.94 (3H, s, —OCH$_3$), 2.33 (2H, dd, J=4.4 and 2.6 Hz, H-6'), 1.41 and 1.31 (2×6H, 2 s, 4×—CH$_3$).

4-[(E)-(5,6-Dihydro-5,5-dimethyl-8-((Z)-3-methyl-3-hydroxyl-1-buten-1-yl)-2-naphthalenyl)ethenyl]benzoic acid Methyl 4-[(E)-(5,6-dihydro-5,5-dimethyl-8-((Z)-3-methyl-3-hydroxy-1-buten-1-yl)-2-naphthalenyl)ethenyl]benzoate (0.135 g, 0.335 mmol) was saponified as described in Example 1 and afforded the title material (0.083 g, 64%) as a white fluffy solid.

IR (nujol) $v_{max}$ (cm$^{-1}$): 2924, 2855, 1681 (C=O), 1604.

$^1$H NMR 400 MHz (DMSO-d$_6$) δ (ppm): 7.92 (2H, d, J=8.1 Hz, H-2 and H-6), 7.72 (2H, d, J=8.2 Hz, H-3 and H-5), 7.52 (1H, br d, J=8.0 Hz, H-3'), 7.40–7.36 (3H, m, vinyl H, H-1' and H-4'), 7.21 (1H, d, J=16.4 Hz, vinyl H), 6.03 (1H, br d, J=12.5 Hz, —CH̲=CH(CH$_3$)$_2$OH), 5.89 (1H, br s, H-7'), 5.87 (1H, d, J=12.5 Hz, —CH=CH̲(CH$_3$)$_2$OH), 2.25 (2H, br s, H-6'), 1.25 (12H, s, 4×—CH$_3$).

| Anal. Calcd. for C$_{26}$H$_{28}$O$_3$: | C 80.38; H 7.27. |
|---|---|
| Found: | C 80.47; H 6.96. |

Example 3

Reference Compound A

4-[(E)-(5,6-Dihydro-5,5-dimethyl-7-methyl-8-(3,3-dimethyl-1-butyn-1-yl)-2-naphthalenyl)ethenyl]benzoic acid

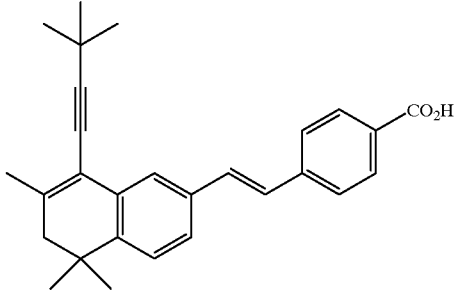

1,2,3,4-Tetrahydro-4,4-dimethyl-2-methyl-1-oxo-7-bromo-naphthalene

To a suspension of potassium hydride (35% in oil, 4.6 g, 40 mmol) in ethyl ether (50 mL) was added dropwise a solution of 1,2,3,4-tetrahydro-4,4-dimethyl-1-oxo-7-bromo-naphthalene (U.S. Pat. No. 5,618,839 and EP 661,259 A1) (5.06 g, 20 mmol) in ether (10 mL). The mixture was stirred at room temperature for 2 hours, then cooled down to −30° C. Methyl triflate (3.4 mL, 30 mmol) was added and the mixture was stirred at −30° C. for 1 hour and 30 minutes at room temperature. The mixture was cooled down to 0° C. and 1N hydrochloric acid was slowly added. The organic phase was separated and the aqueous phase was extracted with ethyl ether. The combined organic phases were washed with water, saturated sodium bicarbonate, brine, dried over anhydrous magnesium sulfate, filtered and concentrated. The residue was purified by silica gel chromatography (4.5×15 cm, 30 to 100% hexane/toluene) and triturated in hexane (3.9 g, 73%) as a white solid.

IR (KBr) $v_{max}$ (cm$^{-1}$): 2960, 2915, 2860, 1685 (C=O).

$^1$H NMR 400 MHz (CDCl$_3$) δ (ppm): 8.12 (1H, d, J=2.2 Hz, H-8), 7.62 (1H, dd, J=8.4 and 2.2 Hz, H-6), 7.30 (1H, d, J=8.4 Hz, H-5), 2.87–2.78 (1H, m, H-2), 1.92–1.86 (2H, m, H-3), 1.42 and 1.38 (2×3H, 2 s, 4-CH$_3$), 1.26 (3H, d, J=6.6 Hz, 2-CH$_3$).

| Anal. Calcd. for C$_{13}$H$_{15}$BrO: | C 58.44; H 5.66. |
|---|---|
| Found: | C 58.59; H 5.62. |

Methyl 4-[[(E)-(5 6,7,8-tetrahydro-5 5-dimethyl-7-methyl-8-oxo)-2-naphthalenyl]vinyl]benzoate A solution of 1,2,3,4-tetrahydro-4,4-dimethyl-2-methyl-1-oxo-7-bromo-naphthalene (0.267 g, 1.0 mmol), methyl 4-vinyl-benzoate (0.245 g, 1.5 mmol), palladium(II) acetate (12 mg), tetrabutylammonium chloride monohydrate (0.292 g, 1.05 mmol) and sodium bicarbonate (0.210 g, 2.5 mmol) was degassed and then heated to 70° C. for 6 hours and stirred overnight at room temperature. The mixture was diluted with ethyl acetate and washed with water (2×20 mL), saturated sodium bicarbonate, brine, dried over anhydrous magnesium sulfate, filtered and concentrated. The residue was purified by silica gel chromatography (3×15 cm, dichloromethane) and triturated in hexane to give the title material (0.270 g, 78%) as a white solid.

m.p.: 157° C.

IR (KBr) $v_{max}$ (cm$^{-1}$): 2960, 2930, 2865, 1710, 1685 (C=O), 1600.

$^1$H NMR 400 MHz (CDCl$_3$) δ (ppm): 8.17 (1H, d, J=2.0 Hz, H-1'), 8.04 (2H, d, J=8.4 Hz, H-2 and H-6), 7.69 (1H, dd, J=8.2 and 2.0 Hz, H-3'), 7.58 (2H, d, J=8.4 Hz, H-3 and H-5), 7.44 (1H, d, J=8.2 Hz, H-4'), 7.24 (1H, d, J$_{AB}$=16.4 Hz, vinyl H), 7.20 (1H, d, J$_{AB}$=16.4 Hz, vinyl H).3.94 (3H, s, —OCH$_3$), 2.91–2.81 (1H, m, H-7'), 1.94 (2H, d, J=9.0 Hz, H-6'), 1.45 and 1.41 (2×3H, 2 s, 5'-CH$_3$), 1.29 (3H, d, J=6.6 Hz, 7'-CH$_3$).

| Anal. Calcd. for C$_{23}$H$_{24}$O$_3$: | C 79.28; H 6.94. |
|---|---|
| Found: | C 78.99; H 6.92. |

Methyl 4-[(E)-[5,6-dihydro-5,5-dimethyl-7-methyl-8-trifluoromethanesulfonyloxy-2-naphthalenyl]ethenyl]benzoate A solution of methyl 4-[[(E)-(5,6,7,8-tetrahydro-5,5-dimethyl-7-methyl-8-oxo)-2-naphthalenyl]vinyl]benzoate (0.245 g, 0.7 mmol) in tetrahydrofuran (6 mL) was treated with a solution of lithium bis(trimethylsilyl)amide (1.0M in tetrahydrofuran, 1.04 mL, 1.04 mmol) at −78° C. and the resulting mixture was stirred for 50 minutes. A solution of 2-[N,N-bis(trifluoromethylsulfonyl)amino]pyridine (327 mg, 0.91 mmol) in tetrahydrofuran (3.5 mL) was added dropwise and the mixture was allowed to reach room temperature overnight. The mixture was then cooled down to 0° C. and water was added followed by ethyl acetate. The organic phase was separated, washed with brine, dried over anhydrous magnesium sulfate, filtered and concentrated.

The residue was purified by silica gel chromatography (2×15 cm, toluene) and triturated in hexanes at 0° C. to give the title material (0.245 g, 85%) as a white solid.

IR (KBr) $v_{max}$ (cm$^{-1}$): 2980, 2960, 1720, (C=O), 1610.

$^1$H NMR 400 MHz (CDCl$_3$) δ (ppm): 8.04 (2H, d, J=8.3 Hz, H-2 and H-6), 7.58 (2H, d, J=8.3 Hz, H-3 and H-5), 7.52 (1H, br s, H-1'), 7.44 (1H, br d, J=8.0 Hz, H-3'), 7.30 (1H, d, J=8.0 Hz, H-4'), 7.20 (1H, d, J=16.3 Hz, vinyl H), 7.11 (1H, d, J=16.3 Hz, vinyl H), 3.94 (3H, s, —OCH$_3$), 2.35 (2H, s, H-6'), 2.02 (3H, s, —CH$_3$-7'), 1.33 (6H, s, 2×—CH$_3$-5').

| Anal. Calcd. for C$_{24}$H$_{23}$F$_3$O$_5$S: | C 59.99; H 4.83. |
|---|---|
| Found: | C 60.15; H 4.80. |

Methyl 4-[(E)-(5,6-dihydro-5,5-dimethyl-7-methyl-8-(3,3-dimethyl-1-butyn-1-yl)-2-naphthalenyl)ethenyl]benzoate Methyl 4-[(E)-[5,6-dihydro-5,5-dimethyl-7-methyl-8-trifluoromethanesulfonyloxy-2-naphthalenyl]ethenyl] benzoate (0.220 g, 0.458 mmol) and 3,3-dimethyl-1-butyne (2×0.141 mL, 2×1.15 mmol) were reacted as described in Example 1 and afforded the title material (0.148 g, 78%) as a white solid.

IR (KBr) $v_{max}$ (cm$^{-1}$): 2980, 2910, 2870, 1718, (C=O), 1610.

$^1$H NMR 400 MHz (CDCl$_3$) δ (ppm): 8.03 (2H, d, J=8.4 Hz, H-2 and H-6), 7.84 (1H, d, J=1.7 Hz, H-1'), 7.56 (2H, d, J=8.4 Hz, H-3 and H-5), 7.34 (1H, dd, J=7.8 and 1.7 Hz, H-3'), 7.27 (1H, d, J=7.8 Hz, H-4'), 7.23 (1H, d, J=16.3 Hz, vinyl H), 7.12 (1H, d, J=16.3 Hz, vinyl H), 3.94 (3H, s, —OCH$_3$), 2.25 (2H, s, H-6'), 2.14 (3H, s, —CH$_3$7'), 1.43 (9H, s, —tBu), 1.26 (6H, s, 2×—CH$_3$).

| Anal. Calcd. for C$_{29}$H$_{32}$O$_2$: | C 84.42; H 7.82. |
|---|---|
| Found: | C 84.05; H 7.91. |

4-[(E)-(5,6-Dihydro-5,5-dimethyl-7-methyl-8-(3,3-dimethyl-1-butyn-1-yl)-2-naphthalenyl)ethenyl]benzoic acid Methyl 4-[(E)-(5,6-dihydro-5,5-dimethyl-7-methyl-8-(3,3-dimethyl-1-butyn-1-yl)-2-naphthalenyl)ethenyl]benzoate (0.130 g, 0.315 mmol) was saponified as described in Example 1 and afforded the title material (0.125 g, 100%) as a white fluffy solid.

IR (KBr) $v_{max}$ (cm$^{-1}$): 2975, 2960, 1670 (C=O), 1605.

$^1$H NMR 400 MHz (DMSO-d$_6$) δ (ppm): 12.90 (1H, s, —CO$_2$H), 7.94 (2H, d, J=7.9 Hz, H-2 and H-6), 7.71 (2H, d, J=7.9 Hz, H-3 and H-5), 7.71 (1H, br s, H-1'), 7.49 (1H, d, J=8.0 Hz, H-3'), 7.40 (1H, d, J=16.4 Hz, vinyl H), 7.32 (1H, d, J=8.0 Hz, H-4'), 7.19 (1H, d, J=16.4 Hz, vinyl H), 2.24 (2H, s, H-6'), 2.09 (3H, s, —CH$_3$7'), 1.39 (9H, s, —tBu), 1.20 (6H, s, 2×—CH$_3$).

| Anal. Calcd. for C$_{28}$H$_{30}$O$_2$.0.2 H$_2$O: | C 83.63; H 7.62. |
|---|---|
| Found: | C 83.52; H 7.50. |

Example 4

Reference Compound C

4-[(E)-(5,6-Dihydro-5,5-dimethyl-8-((Z)-3,3-dimethyl-1-buten-1-yl)-2-naphthalenyl)ethenyl] benzoic acid

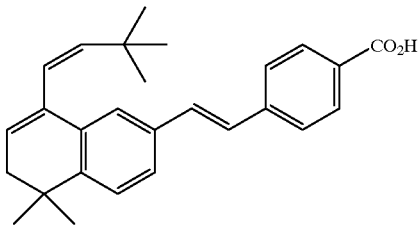

Methyl 4-[(E)-(5,6-dihydro-5,5-dimethyl-8-((Z)-3,3dimethyl-1-buten-1-yl)- 2-naphthalenyl)ethenyl]benzoate A solution of methyl 4-[(E)-(5,6-dihydro-5,5-dimethyl-8-(3,3-dimethyl-1-butyn-1-yl)-2-naphthalenyl)ethenyl] benzoate prepared in Example 1 (4.39 g, 11.02 mmol) in pyridine (40 mL) was stirred under a hydrogen atmosphere (rubber balloon) in the presence of 5% Pd/BaSO$_4$ (2.0 g) for 16 hours. More catalyst (1.0 g) was then added and the hydrogenation was resumed for another 8 hours. The reaction mixture was diluted with ethyl ether and filtered through celite. The filtrate was washed with water, 1N hydrochloric acid and brine. The organic phase was dried over anhydrous magnesium sulfate, filtered and concentrated. The residue was triturated in hexane and collected to give the title material (3.0 g, 68%).

IR (CH$_2$Cl$_2$) $v_{max}$ (cm$^{-1}$): 2950, 1705 (C=O), 1595.

$^1$H NMR 400 MHz (CDCl$_3$) δ (ppm): 8.03 (2H, d, J=8.4 Hz, H-2 and H-6), 7.58 (2H, d, J=8.4 Hz, H-3 and H-5), 7.41 (2H, m, H-1' and H-3' or H-4'), 7.34 (1H, m, H-3' or H-4'), 7.22 (1H, d, J=16.3 Hz, vinyl H), 7.08 (1H, d, J=16.3 Hz, vinyl H), 6.00 (1H, dq, J=12.4 and 2.2 Hz, —CH=CH—tBu), 5.84 (1H, td, J=4.4 and 1.8 Hz, H-7'), 5.73 (1H, d, J=12.4 Hz, —CH=CH—tBu), 3.94 (3H, s, —OCH$_3$), 2.30 (2H, dd, J=4.4 and 2.7 Hz, H-6'), 1.31 (6H, s, 2×—CH$_3$), 1.11 (9H, s, —tBu).

4-[(E)-(5,6-Dihydro-5,5-dimethyl-8-((Z)-3,3-dimethyl-1-buten-1-yl)-2-naphthalenyl)ethenyl]benzoic acid A solution of methyl 4-[(E)-(5,6-dihydro-5,5-dimethyl-8-((Z)-3,3-dimethyl-1-buten-1-yl)-2-naphthalenyl)ethenyl] benzoate (3.0 g, 7.49 mmol) in tetrahydrofuran (60 mL) and ethanol (30 mL) was treated with 4N sodium hydroxide (9.36 mL, 37.6 mmol) and stirred for 30 hours. The reaction mixture was diluted with water and acidified to pH 2 with concentrated hydrochloric acid. The acid precipitated and was extracted into ethyl acetate. The organic extracts were washed with brine, dried over anhydrous magnesium sulfate, filtered and concentrated. The crude residue was dissolved in dichloromethane (75 mL) and ethanol (50 mL), filtered through a sintered glass and the filtrate was concentrated. The title material precipitated and was collected and dried to give a white solid (2.455 g, 85%).

IR (nujol) $v_{max}$ (cm$^{-1}$): 2915, 2845, 1680 (C=O), 1595.

$^1$H NMR 400 MHz (DMSO-d$_6$) δ (ppm): 7.91 (2H, d, J=8.2 Hz, H-2 and H-6), 7.72 (2H, d, J=8.2 Hz, H-3 and H-5), 7.54 (1H, br d, J=8.0 Hz, H-3'), 7.42–7.34 (3H, m, vinyl H, H-1' and H-4'), 7.19 (1H, d, J=16.4 Hz, vinyl H), 6.01 (1H, br d, J=12.4 Hz, —CH=CH—tBu), 5.81 (1H, br s, H-7'), 5.70 (1H, d, J=12.4 Hz, —CH=CH—tBu), 2.26 (2H, br s, H-6'), 1.25 (6H, s, 2×—CH$_3$), 1.07 (9H, s, —tBu).

| Anal. Calcd. for $C_{27}H_{30}O_2$: | C 83.90; H 7.82. |
|---|---|
| Found: | C 83.27; H 7.73. |

Example 5

Reference Compound B

4-[(E)-(5,6-Dihydro-5,5-dimethyl-8-((Z)-3-methyl-3-ethyl-1-penten-1-yl)-2-naphthalenyl)ethenyl]benzoic acid

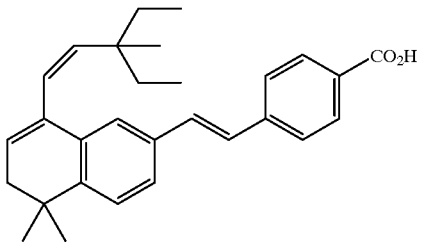

(Iodomethyl)triphenylphosphonium iodide

A solution of triphenylphosphine (6.56 g, 25 mmol) and diiodomethane (8.7 g, 32.5 mmol) in benzene (25 mL) was heated at 60° C. for 20 hours. The mixture was cooled to room temperature and the precipitated salt was collected by filtration, washed with benzene and dried to give the title material (7.38 g, 56%).

(Z)-3-Ethyl-3-methyl-1-iodo-1-pentene

A suspension of (iodomethyl)triphenylphosphonium iodide (0.530 g, 1 mmol) in tetrahydrofuran (3 mL) was treated dropwise at room temperature with sodium bis(trimethylsilyl)amide (1 mL, 1M solution in THF, 1 mmol) for 2–3 minutes. The solution was then cooled to −78° C. and a solution of 2-ethyl-2-methyl-butanal (0.100 g, 0.88 mmol) in tetrahydrofuran was added dropwise. The cooling bath was removed and stirring continued at room temperature for 1 hour. The reaction mixture was diluted with hexane, filtered and evaporated. The crude compound was purified by silica gel chromatography (hexane) and afforded the title compound (0.130 g, 62%).

$^1$H NMR 400 MHz (CDCl$_3$) δ (ppm): 0.84 (6H, t, J=7.5 Hz, 2×—CH$_2$C$\underline{H}$$_3$), 1.15 (3H, s, —CH$_3$), 1.47 and 1.65 (2×2H, 2m, 2×—C$\underline{H}$$_2$—H$_3$), 6.20 (1H, d, J=8.5 Hz, —C$\underline{H}$=CHI), 6.36 (1H, d, J=8.5 Hz, =CHI).

(Z)-3-Ethyl-3-methyl-1-(tributylstannyl)-1-pentene

A solution of (Z)-3-ethyl-3-methyl-1-iodo-1-pentene (0.660 g, 2.78 mmol) and bis(tributyltin) (3.22 g, 5.55 mmol) in dioxane was heated at 85° C. for 16 hours in the presence of tetrakis(triphenylphosphine)palladium(0) (50 mg). The solvent was evaporated and the residue was purified on silica gel chromatography (hexane) to give the title compound (0.440 g, 40%) contaminated with 11% of the trans isomer.

$^1$H NMR 400 MHz (CDCl$_3$) δ (ppm): 0.75–0.97 and 1.27–1.53 (40H, 4 sets of m, 3×—(CH$_2$)$_3$CH$_3$, 2×—CH$_2$CH$_3$ and —CH$_3$), 5.71 (1H, d, J=14.2 Hz, —CH=), 6.45 (1H, d, J=14.2 Hz, =CH—Sn).

Methyl 4-[(E)-(5,6-dihydro-5,5-dimethyl-8-((Z)-3-methyl-3-ethyl-1-penten-1-yl)-2-naphthalenyl)ethenyl]benzoate A solution of methyl 4-[(E)-[5,6-dihydro-5,5-dimethyl-8-trifluoromethanesulfonyloxy-2-naphthalenyl]ethenyl]benzoate (0.320 g, 0.685 mmol) and (Z)-3-ethyl-3-methyl-1-(tributylstannyl)-1-pentene (0.440 g, 1.1 mmol), lithium chloride (87 mg, 2.06 mmol) and tetrakis(triphenylphosphine)palladium(0) (30 mg) in dioxane was heated at 95° C. for 20 hours. The solvent was evaporated and the crude residue was purified on silica gel chromatography (5% ethyl acetate/hexane) to give the title material (0.252 g, 86%) as a colorless foam. Crystallization in hexane at −15° C. gave the pure cis isomer (0.040 g) free of the trans isomer but contaminated with 10% of the 8-unsubstituted analog.

$^1$H NMR 400 MHz (CDCl$_3$) δ (ppm): 0.89 (6H, t, J=7.4 Hz, 2×—CH$_2$C$\underline{H}$$_3$), 0.97 (3H, s, —CH$_3$), 1.31 (6H, s, 2×—CH$_3$), 1.26–1.50 (4H, m, 2×—C$\underline{H}$$_2$CH$_3$), 2.29 (2H, dd, J=4.4 and 2.7 Hz, H-6'), 3.93 (3H, s, —OCH$_3$), 5.53 (1H, d, J=12.7 Hz, =C$\underline{H}$—C(Et)$_2$CH$_3$), 5.83 (1H, dd, J=4.5 and 1.9 Hz, H-7'), 6.14 (1H, dq, J=12.7 and 2.3 Hz, —C$\underline{H}$=CH—C(Et)$_2$CH$_3$), 7.08 and 7.20 (2×1H, 2 d, J=16.3 Hz, vinyl H), 7.33 (1H, d, J=7.9 Hz, H-4'), 7.38 (1H, dd, J=7.8 and 1.8 Hz, H-3'), 7.47 (1H, d, J=1.5 Hz, H-1'), 7.56 (2H, d, J=8.3 Hz, H-3 and H-5), 8.02 (2H, d, J=8.4 Hz, H-2 and H-6).

4-[) (E)-(5,6-Dihydro-5,5-dimethyl-8-((Z)-3-methyl-3-ethyl-1-penten-1-yl)-2-naphthalenyl)ethenyl]benzoic acid Methyl 4-[(E)-(5,6-dihydro-5,5-dimethyl-8-((Z)-3-methyl-3-ethyl-1-penten-1-yl)-2-naphthalenyl)ethenyl]benzoate (0.042 g, 0.1 mmol) was saponified as described in Example 1 and afforded the title compound (0.018 g, 43%).

IR (nujol) $v_{max}$ (cm$^{-1}$): 2924, 2855, 1687 (C=O).

$^1$H NMR 400 MHz (DMSO-d$_6$) δ (ppm): 7.92 (2H, d, J=8.2 Hz, H-2 and H-6), 7.70 (2H, d, J=8.2 Hz, H-3 and H-5), 7.50 (1H, d, J=7.9 Hz, H-3'), 7.41 (1H, br s, H-1'), 7.37 (1H, d, vinyl H), 7.36 (1H, d, H-4'), 7.17 (1H, d, J=16.4 Hz, vinyl H), 6.17 (1H, br dq, J=12.7 and 2.0 Hz, —C$\underline{H}$=CH—C(Et)$_2$CH$_3$), 5.79 (1H, br q, J=1.4 Hz, H-7'), 5.50 (1H, d, J=12.7 Hz, =C$\underline{H}$—C(Et)$_2$CH$_3$), 2.26 (2H, br d, J=2.9 Hz, H-6'), 1.38 (4H, m, 2×—C$\underline{H}$$_2$CH$_3$), 1.25 (6H, s, 2×—CH$_3$), 0.91 (3H, s, —CH$_3$), 0.82 (6H, t, J=7.3 Hz, 2×—CH$_2$C$\underline{H}$$_3$).

MS: 413.2 (MH)$^+$.

Example 6

Reference Compound D

4-[(E)-(5,6-Dihydro-5,5-dimethyl-8-(1-methyl-1-ethane-thio)-2-naphthalenyl)ethenyl]benzoic acid

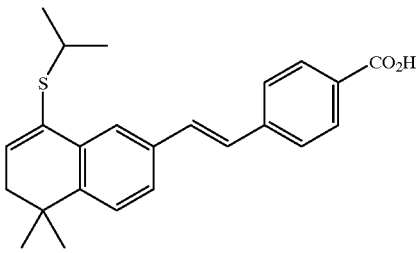

Methyl 4-[(E)-(5,6-dihydro-5,5-dimethyl-8-((Z)-3,3dimethyl-1-buten-1-yl)- 2-naphthalenyl)ethenyl]benzoate To a stirred solution of methyl 4-[[(E)-(5,6,7,8-tetrahydro-5,5-dimethyl-8-oxo)-2-naphthalenyl]vinyl]

benzoate (U.S. Pat. 5,618,839 and EP 661,259 A1) (1.0 g, 3 mmol) in tetrahydrofuran (30 mL) was added dropwise titanium chloride (1M in dichloromethane, 3 mL, 3 mmol). The resulting dark solution was stirred for 5 minutes and a solution of isopropylthiol (420 μL, 0.343 g, 4.5 mmol) and triethylamine (0.607 g, 0.84 mL, 6 mmol) in tetrahydrofuran (2 mL) was added again. The reaction mixture was stirred at room temperature for 20 hours. Mercuric trifluoroacetate (1.3 g, 3 mmol) and lithium carbonate (1.3 g, 18 mmol) were then added at the same time and the mixture was stirred for 5 minutes. Silica gel (20 mL) was added and the mixture was filtered after stirring for 2 minutes. The solid was washed with dichloromethane (100 mL) and the filtrate was concentrated. The residue was purified on silica gel chromatography (dichloromethane) and afforded the title compound which was recrystallized from ethanol (0.956 g, 88%).

$^1$H NMR 400 MHz (CDCl$_3$) δ (ppm): 8.04 (2H, d, J=8.4 Hz, H-2 and H-6), 7.98 (1H, d, J=1.8 Hz, H-1'), 7.60 (2H, d, J=8.3 Hz, H-3 and H-5), 7.43 (1H, dd, J=8.0 and 1.8 Hz, H-3'0, 7.35 (1H, d, J=7.9 Hz, H-4'), 7.26 and 7.14(2×1H, 2 d, J=16.3 Hz, vinyl H), 6.39 (1H, t, J=4.7 Hz, H-7'), 3.94 (3H, s, —OMe), 3.20 (1H, m, J=6.7 Hz, —CH(CH$_3$)$_2$), 2.34 (2H, d, J=4.7 Hz, H-6'), 1.31 (6H, s, 2×—CH$_3$), 1.31 (6H, d, J=6.6 Hz, —CH(CH$_3$)$_2$).

4-[(E)-(5,6-Dihydro-5,5-dimethyl-8-(1-methyl-1-ethanethio)-2-naphthalenyl)ethenyl]benzoic acid Methyl 4-[(E)-(5,6-dihydro-5,5-dimethyl-8-(1-methyl-1-ethanethio)-2-naphthalenyl)ethenyl]benzoate (0.729 g, 1.857 mmol) was saponified as described in Example 1 and afforded the title material (0.675 g, 96%) as a white solid.

IR (KBr) ν$_{max}$ (cm$^{-1}$):3435, 2957, 1682 (C=O), 1603.

$^1$H NMR 400 MHz (DMSO-d$_6$) δ (ppm): 7.93 (2H, d, J=8.4 Hz, H-2 and H-6), 7.84 (1H, d, J=1.6 Hz, H-1'), 7.73 (2H, d, J=8.4 Hz, H-3 and H-5), 7.59 (1H, dd, J=8.0 and 1.6 Hz, H-3'), 7.47 (1H, d, J=16.4 Hz, vinyl H), 7.38 (1H, d, J=8.0 Hz, H-4'), 7.25 (1H, d, J=16. 4 Hz, vinyl H), 6.34 (1H, t, J=4.7 Hz, H-7'), 3.21 (1H, m, J=6.6 Hz, —C$\underline{H}$(Me)$_2$), 2.30 (2H, d, J=4.7 Hz, H-6'), 1.25 (6H, s, 2×—CH$_3$), 1.24 (6H, d, J=6.5 Hz, —CH(C$\underline{H}$$_3$)$_2$).

MS: 377.07 (M−H)$^-$.

| | |
|---|---|
| Anal. Calcd. for C$_{24}$H$_{26}$O$_2$S: | C 76.15; H 6.92. |
| Found: | C 75.89; H 6.50. |

We claim:
1. A retinoid compound of formula I

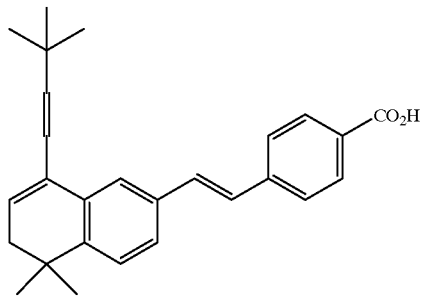

or a nontoxic pharmaceutically acceptable salt, physiologically hydrolyzable ester or solvate thereof.

2. A retinoid compound of formula II

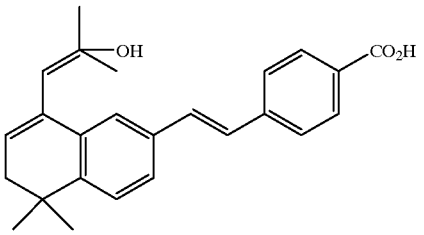

or a nontoxic pharmaceutically acceptable salt, physiologically hydrolyzable ester or solvate thereof.

3. A pharmaceutical composition comprising a therapeutically effective amount of a retinoid compound of claim 1 and a pharmaceutically acceptable carrier or excipient.

4. A pharmaceutical composition comprising a therapeutically effective amount of a retinoid compound of claim 2 and a pharmaceutically acceptable carrier or excipient.

5. A method for inhibiting tumor growth in a mammalian host which comprises administering to said host a tumor-growth inhibiting amount of a compound of claim 1.

6. A method for inhibiting tumor growth in a mammalian host which comprises administering to said host a tumor-growth inhibiting amount of a compound of claim 2.

* * * * *

UNITED STATES PATENT AND TRADEMARK OFFICE
CERTIFICATE OF CORRECTION

PATENT NO.   : 6,194,601 B1
DATED        : February 27, 2001
INVENTOR(S)  : Anne Marinier et al.

It is certified that error appears in the above-identified patent and that said Letters Patent is hereby corrected as shown below:

<u>Title page,</u>
Item [57], ABSTRACT, the portion of formula II reading 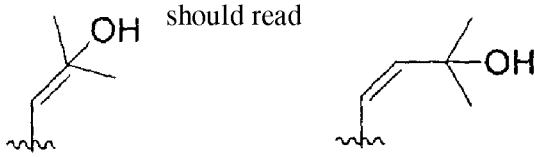 should read <u>Column 28,</u>
Line 25, the portion of formula II reading 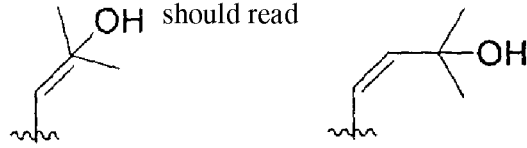 should read Signed and Sealed this Second Day of September, 2003

JAMES E. ROGAN
*Director of the United States Patent and Trademark Office*